US007189358B2

(12) United States Patent
Beach et al.

(10) Patent No.: US 7,189,358 B2

(45) Date of Patent: Mar. 13, 2007

(54) INTEGRATED MICROPUMP ANALYSIS CHIP AND METHOD OF MAKING THE SAME

(75) Inventors: Robert A. Beach, Altadena, CA (US); Robert P. Strittmatter, Pasadena, CA (US); Thomas C. McGill, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 782 days.

(21) Appl. No.: 09/923,582

(22) Filed: Aug. 7, 2001

(65) Prior Publication Data

US 2002/0071785 A1 Jun. 13, 2002

Related U.S. Application Data

(60) Provisional application No. 60/223,672, filed on Aug. 8, 2000.

(51) Int. Cl.

| | |
|---|---|
| ***G01N 15/06*** | (2006.01) |
| ***G01N 33/00*** | (2006.01) |
| ***G01N 33/48*** | (2006.01) |
| ***H01L 21/302*** | (2006.01) |
| ***E03B 1/00*** | (2006.01) |

(52) U.S. Cl. ......................... 422/68.1; 422/50; 422/61; 422/63; 422/100; 422/81; 422/82.05; 422/103; 422/104; 436/43; 436/174; 73/1.01; 73/1.02; 73/1.16; 73/1.69; 73/1.71; 438/689; 137/1; 137/255; 417/1

(58) Field of Classification Search .................. 422/50, 422/61, 63, 68.1, 81, 82.05, 100, 103, 104; 436/43, 174; 73/1.01, 1.02, 1.16, 1.69, 1.71; 438/689; 137/1, 255; 417/1

See application file for complete search history.

(56) References Cited

U.S. PATENT DOCUMENTS

| | | | | |
|---|---|---|---|---|
| 5,653,939 | A * | 8/1997 | Hollis et al. | 422/50 |
| 5,846,396 | A * | 12/1998 | Zanzucchi et al. | 204/601 |
| 6,177,057 | B1 * | 1/2001 | Purdy | 423/409 |
| 6,306,273 | B1 * | 10/2001 | Wainright et al. | 204/454 |
| 6,394,759 | B1 * | 5/2002 | Parce | 417/48 |
| 6,444,474 | B1 * | 9/2002 | Thomas et al. | 436/146 |
| 6,495,852 | B1 * | 12/2002 | Mouri | 257/21 |
| 6,579,068 | B2 * | 6/2003 | Bridger et al. | 417/53 |
| 6,655,923 | B1 * | 12/2003 | Lisec et al. | 417/92 |

* cited by examiner

*Primary Examiner*—Brian Sines

(74) *Attorney, Agent, or Firm*—Daniel L. Dawes; Myers Dawes Andras & Sherman

(57) ABSTRACT

An integrated micropump or a plurality of integrated micropumps are communicated to a plurality of analysis chambers. A plurality of integrated analysis chambers include integrated analysis devices to test a fluid for an analyte. The micropumps continuously or periodically pump the fluid into the analysis chambers and flush the analysis chambers after analysis of the analyte. In one embodiment, the analysis device comprises an integrated LED and an integrated optical detector. The LED and detector are tuned to an optical absorption line of the analyte. The micropumps are composed of nitrides of B, Al, Ga, In, Tl or combinations thereof and fabricated using photoelectrochemical techniques. The analysis chambers, and micropumps including the analysis devices are simultaneously fabricated during which fabrication of the micropumps and the analysis devices are masked from the photoelectrochemical techniques.

16 Claims, 2 Drawing Sheets

INTEGRATED MICROPUMP ANALYSIS CHIP AND METHOD OF MAKING THE SAME

RELATED APPLICATIONS

The present application is related to U.S. Provisonal patent application Ser. No. 60/223,672, filed on Aug. 8, 2000.

BACKGROUND OF THE INVENTION

1. Field of the Invention

The invention relates to the field of micromachined chemical analysis systems.

2. Description of the Prior Art

The micromaching of devices for microfluidic circuits is well known. Biological or chemical assay systems developed on a chip are also well known. However, the economic and practical design whereby micropumps can be combined with the assay chambers and analytic device in an assembly of such micropumps, assay chambers and analytic devices has not yet been solved.

What is needed is a systems approach which is adapted to integrating microfluidic pumping devices with pressure sensors, optical sensors and chemical sensors into a single chip.

BRIEF SUMMARY OF THE INVENTION

The invention is defined as an apparatus comprising a plurality of integrated micropumps for pumping fluid to be analyzed. An analysis chamber or a plurality of analysis chambers are communicated to the plurality of micropumps. The plurality of analysis chambers include integrated analysis devices to test the fluid in the analysis chambers for an analyte.

The plurality of micropumps pump the fluid into the plurality of analysis chambers and flush the plurality of analysis chambers after analysis of the analyte in the fluid. In one embodiment the plurality of micropumps continuously pump the fluid into the plurality of analysis chambers and continuously flush the plurality of analysis chambers after analysis of the analyte in the fluid.

In one embodiment the analysis device in at least one of the plurality of analysis chambers comprises an integrated LED and an integrated optical detector. The integrated LED and integrated optical detector are tuned to an optical absorption line of the analyte. In another embodiment a plurality of integrated pressure sensors are included in the micropumping chamber. In still another embodiment an integrated chemical or chem-FET is included in the probe chamber so that the chemical shift of the surface potential due to the analyte interaction with the gate of the FET leads to a shift in electrical characteristics of the chem-FET.

The invention is also characterized as a method of fabricating an apparatus of microanalysis of fluidic analytes comprising the steps of fabricating a plurality of micropumps composed of nitrides of B, Al, Ga, In, Tl or combinations thereof using photoelectrochemical techniques, and simultaneously or separately fabricating the micropumps for pumping the fluid to be analyzed. The method continues with the step of simultaneously fabricating a plurality of analysis chambers communicated to the plurality of micropumps including analysis devices to test the fluid in the analysis chambers for an analyte. The analysis devices are masked from the photoelectrochemical techniques used during the fabrication of the plurality of micropumps and of the analysis chambers.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
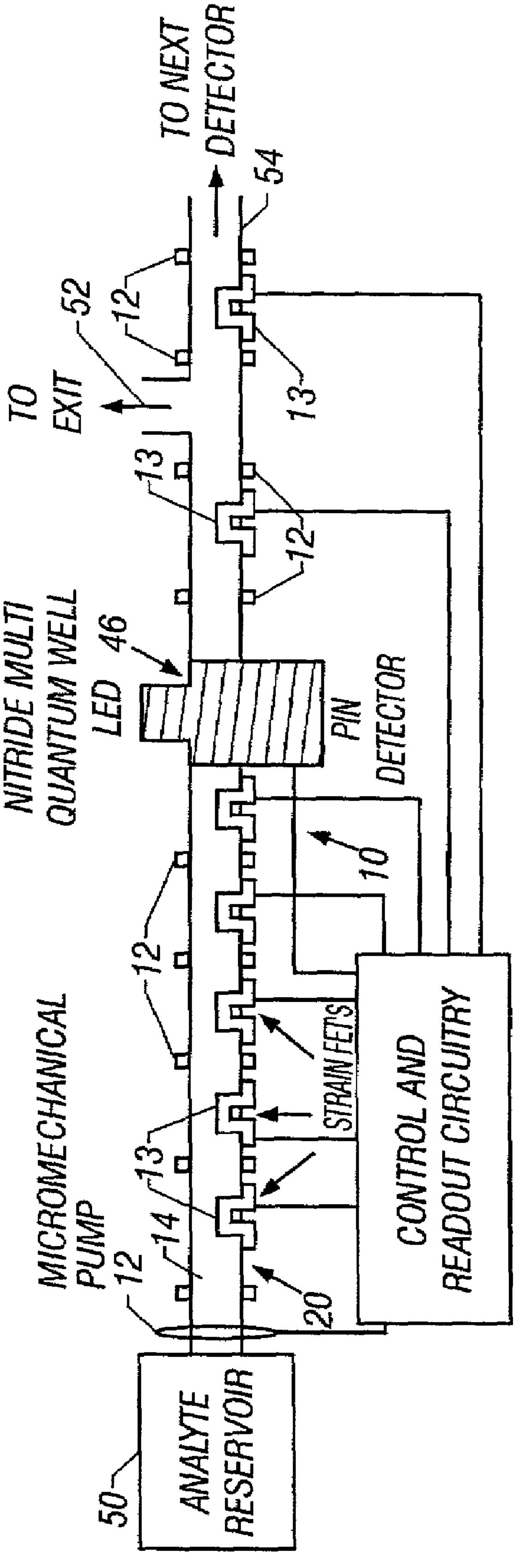
FIG. 1 is a block diagram of the general concept of the invention showing a system or biochip in which a pumping chamber is integrated with a plurality of probes and where the fluidic channeling decisions or flows are determined based on the measured properties of the analyte.

A plurality of micropumps or a single distributed micropump 12 is communicated to a plurality of analysis chambers 14 in a microchannel 20 as diagrammatically shown in FIG. 1. Pump 12 is shown schematically only in one position, but it must be understood that it may be repeated at different longitudinal positions along microchannel 20 or may be a single peristaltic pump 12 extending the entire length of microchannel 20. The plurality of analysis chambers 14 include analysis devices 13 to test a fluid for an analyte. The micropumps 12 continuously or periodically pump the fluid into the analysis chambers and flush the analysis chambers after analysis of the analyte. In one embodiment, the analysis device 13 comprises an integrated LED and an integrated optical detector described in greater detail in FIG. 2. The LED and detector are tuned to an optical absorption line of the analyte. The micropumps are composed of nitrides of B, Al, Ga, In, Tl or combinations thereof and fabricated using photoelectrochemical techniques. The analysis chambers, micropumps and probe chambers including analysis devices 13 are simultaneously fabricated during which fabrication of the micropumps and probe chambers, the analysis devices 13 are masked from the photoelectrochemical etching techniques.

As again diagrammatically shown in FIG. 1 the invention is comprised of an array or system 10 of micromechanical peristaltic pumps 12 (MMPs) or a single peristaltic pump 12 that extends the length of the microchannel 20. Pump(s) 12 controls the delivery of the fluid (either air or liquid) under investigation to one or a series of analysis chambers 14. The MMPs 12 are also employed to flush the analysis chambers 14 after each test. Chambers 14, which are defined segments in microchannel 20, which may or may not be delineated from each other by means other than position, are designed to provide a location or space in which to probe the fluid for a unique chemical compound (such as insulin), biological entity (such as a particular virus) or a physical parameter such as pressure or temperature. This allows in situ monitoring of fluid chemistry while enabling adjustment of that chemistry via a micropumped delivery system and allows for continuous adjustment of chemical levels within a system of interest. The analysis chambers 14 can utilize any probes 13 of a variety of technologies compatible with microtechnologies, such as a ph metering, pressure or temperature sensing, conventional chem-FETS or optical absorption.

Micropumps 12 employing the highly chemically stable material GaN have been fabricated using a photo-electrochemical (PEG) etch technique that undercuts regions not masked by metallic overlayers. These pumps 12 have been shown to respond to electric fields by contraction along the direction of electric current flow due to the inverse piezoelectric effect. The plurality of micropumps are fabricated according to the description set out in copending application entitled "A METHOD OF MANUFACTURE OF A SUSPENDED NITRIDE MEMBRANE AND A MICROPERISTALTIC PUMP USING THE SAME", U.S. Pat. No. 6,579,068, which is incorporated herein by reference as if set out in its entirety.

Figure 3:
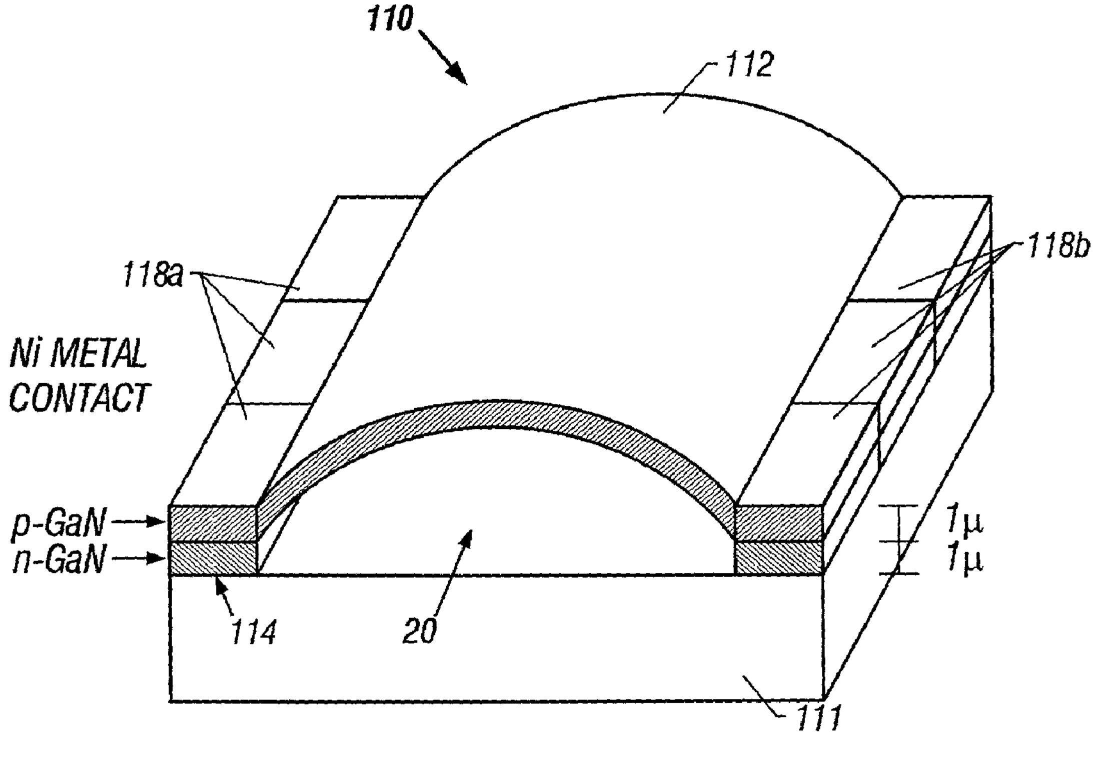
FIG. 3 is an enlarged perspective view of a suspended nitride membrane formed by the PEC process used in the present invention.

The photochemical etching process will be illustrated by briefly describing the fabrication of the micropump in FIG. 3. Greater detail of the process is described in the incorporated application referenced above. An example of the diverse microstructures which can be realized using this etch process includes the GaN microchannel shown in FIG. 3. The microchannel 20 is comprised of an 1 μm thick p-GaN membrane 112 that spans between two long anchoring strips 114 on either side. To fabricate this structure, a series of Ni/Au bars (not shown, but later divided into pads 118*a* and 118*b*) with 100 μm spacing between the bars across was to become channel 20 were patterned on a p-on-n bilayer sample 112, 113 using standard lithographic techniques. The sample was then exposed to the optical photochemical etch process referenced above, during which the unmasked regions which were exposed to UV light between the bars were undercut by the etchant. Etching of n-GaN underlayer 113 proceeded inward from both sides in the direction of the bars. A total undercut channel length of 5 μm etched to completion in roughly 2 hours. Afterward, the metal masks were removed in places, leaving a series of isolated contact pads 118*a* and 118*b* along the anchored sidewalls.

The GaN layers 113 used here were grown by molecular beam epitaxy on c-plane sapphire 111 with no buffer layer. Both the n+ (Si) and the p+ (Mg) epilayers are 1 μm thick, and the growth temperature in each case was 800° C. and 700° C. respectively. Both layers are thought to have carrier concentrations in the range of $10^{18}/cm^3$.

The surface quality of the p-type film 112 does not appear to degrade as a result of the lengthy PEC etch. Furthermore, the underside of the suspended p-GaN film 112 is smooth and featureless. This is in marked contrast to our observations of MOCVD grown p-on-n samples, for which the undersides are rough and coated with etch-resilient whiskers.

As seen in FIG. 3, the p-GaN membrane 112 bows upward after release to relieve inherent stress. A maximum vertical deflection of 9.2 μm is measured at the center of the 100 μm channel width. We believe the primary origin of this stress is the thermal mismatch between the GaN epilayer 113 and the sapphire substrate 111, integrated down from growth temperatures. Measurements of the expanded length of the bowed film correspond to a biaxial compressive strain of $1.0\times10^{-3}$ in the p-GaN layer prior to release. However, we have observed strong evidence that the stress profile in the p-layer 112 is far more complicated: p-GaN cantilever structures relax into a shape which is uniformly curved away from the substrate 111. This bending suggests there are vertical stress gradients in the p-layer 112, perhaps built in at the time of growth as a result of the different lattice constants for Mg and Si doped GaN. A similar adaptation of the process can be used to form microchannel 20.

Similarly, when probes 13 in the system of FIG. 1 are pressure sensors they can be fabricated according to the description set out in copending application entitled "A SEMICONDUCTOR NITRIDE PRESSURE MICROSENSOR AND METHOD OF MAKING AND USING THE SAME", U.S. Pat. No. 6,647,796, which is incorporated herein by reference as if set out in its entirety.

Figure 2:
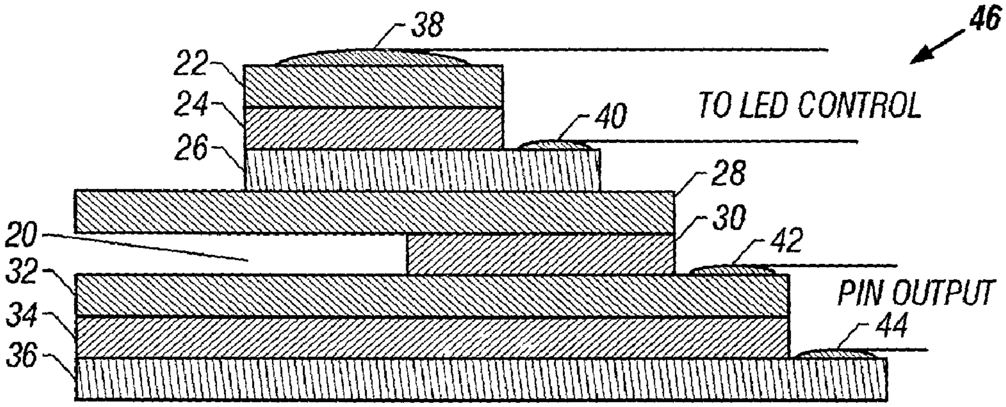
FIG. 2 is a block diagram of a specific embodiment of the concept of the optical detector used in FIG. 1 in which an LED and detector system.

An example of a nitride process technology compatible with PEC is the simultaneous fabrication of a nitride LED and detector system tuned to an absorption line of the chemical of interest is described in FIG. 2. FIG. 2 shows is a side cross-sectional view of such an optical device. Light is generated in an LED comprised of a p type GaN layer 22 disposed on top of a quantum well light emitting layer 24. Layer 24 in turn is disposed on n type GaN layer 26 followed by p type GaN layer 28. Layer 28 forms the top wall of microchannel 20. The peripheral wall is formed by n type GaN layer or frame 30 while the bottom wall of microhannel 20 is formed by p type GaN layer 32. Below layer 32 is an intrinsic GaN absorption layer 34 followed by n type GaN layer 36 so that layers 32, 34 and 36 form the PIN device serving as the optical detector of light generated by the overlying LED device 22, 24, 26. Light from LED device 22, 24, 26 is transmitted through microchannel 20 into PIN 32, 34 and 36 resulting in an optical absorption probe 13. Control of LED device 22, 24, 26 is provided through contacts 38 and 40. Pin 32, 34 and 36 is provided with contacts 42 and 44 for pickup of the detected signal. The entire assembly of FIG. 2 thus comprises an optical probe 46.

The advantage of the configuration of FIG. 2 is that the active components or devices 13 of the analysis chambers 14 can be formed at the same time as the microchannel 20 is formed, and then protected from etching with $SiO_2$ during the etching process.

All of pumps 12, pressure sensors 18, optical probes 46 and any chem-FETs or other sensors are coupled to a conventional logic, computer or control circuit 48 whereby flow of analyte from reservoir 50 into microchannel 20 the system of FIG. 1 is coordinated, timed, sequenced and controlled among branches 52 and 54 according to the application at hand. Any system or control configuration desired may be accommodated with complete generality and the simple system of FIG. 1 is to be expressly understood to be a diagrammatic illustration and not in any sense a limitation of how such systems could be organized.

This invention will allow noninvasive and unintrusive monitoring and control of chemical environments. Combining this with a digital control circuit will allow production of stable chemical environments such as insulin levels in diabetic patients, Ph in acid or base solutions, and countless other applications in which precise chemical control is required.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus comprising:

a single substrate;

a microchannel defined in the substrate;

at least one integrated peristaltic GaN micropump for pumping fluid to be analyzed, operatively and integrally formed about a corresponding portion of the microchannel in the substrate using photo-electro-chemical etch techniques (PEC), which corresponding portion comprises a pumping chamber of the peristaltic micropump;

a plurality of integrated analysis chambers for an analyte communicated to the microchannel and hence to the pumping chamber of the at least one integrated peristaltic micropump; and a plurality of integrated analysis devices integrally manufactured into the substrate using nitride processes compatible with PEC and operatively communicated to the analysis chambers.

2. The apparatus of claim 1 where the integrated analysis chambers are portions of the microchannel.

3. The apparatus of claim 2 where integrated peristaltic micropump comprises a distributed integrated peristaltic micropump comprised of a plurality of micropump sections driven as a single micropump.

4. The apparatus of claim 3 where each of the portions of the microchannel serving as the analysis chamber and each integrated analysis device are pairwise associated with a micropump section of the distributed integrated peristaltic micropump.

5. An apparatus comprising:

a single substrate;

a microchannel defined in the substrate;

at least one integrated GaN peristaltic micropump for pumping fluid to be analyzed operatively and integrally formed about a corresponding portion of the microchannel in the substrate using photo-electro-chemical etch techniques (PEC), which corresponding portion comprises a pumping chamber of the peristaltic micropump;

a plurality of integrated analysis chambers communicated to the microchannel and hence to the pumping chamber of the at least one integrated peristaltic micropump; and a plurality of integrated analysis devices integrally manufactured into the substrate using nitride processes compatible with PEC and operatively communicated to the analysis chambers for an analyte where said micropump comprises:

an electro-deformable GaN membrane;

the substrate disposed below said membrane and coupled thereto, the microchannel defined between said membrane and substrate, said microchannel having a longitudinal axis; and an electrode structure disposed on at least one side of said membrane along side of said microchannel.

6. The apparatus of claim 5 where said electro-deformable membrane is bowed to form a curvature having a symmetrical axis in the direction of said longitudinal axis of said microchannel.

7. The apparatus of claim 5 further comprising a drive circuit coupled to said electrode structure to apply a sequential voltage along said plurality of opposing electrodes to peristaltically deform said electro-deformable membrane in the direction of said longitudinal axis of said microchannel.

8. The apparatus of claim 5 where said electro-deformable membrane consists of p-type GaN.

9. The apparatus of claim 6 where said electro-deformable membrane consists of p-type GaN.

10. An apparatus comprising:

a single substrate;

a microchannel defined in the substrate;

at least one integrated GaN peristaltic micropump for pumping fluid to be analyzed, operativelv and integrally formed about a corresponding portion of the microchannel in the substrate using photo-electro-chemical etch techniques (PEC), which corresponding portion comprises a pumping chamber of the peristaltic micropump;

a plurality of integrated analysis chambers communicated to the microchannel and hence to the pumping chamber of the at least one integrated peristaltic micropump;

a plurality of integrated analysis devices integrally manufactured into the substrate using nitride processes compatible with PEC and operatively communicated to the analysis chambers for an analyte, and two opposing pillars disposed on said substrate between said substrate and said membrane generally aligned in the direction of said longitudinal axis, where said micropump comprises:

an electro-deformable GaN membrane;

a substrate disposed below said membrane and coupled thereto, a microchannel defined between said membrane and substrate, said microchannel having a longitudinal axis; and an electrode structure disposed on at least one side of said membrane along side of said microchannel.

11. The apparatus of claim 10 where said electro-deformable membrane is bowed to form a curvature having a symmetrical axis in the direction of said longitudinal axis of said microchannel.

12. The apparatus of claim 10 further comprising a drive circuit coupled to said electrode structure to apply a sequential voltage along said plurality of opposing electrodes to peristaltically deform said electro-deformable membrane in the direction of said longitudinal axis of said microchannel.

13. The apparatus of claim 10 where said electro-deformable membrane is bowed to form a curvature having a symmetrical axis in the direction of said longitudinal axis of said microchannel and where said electro-deformable membrane is composed of p-type GaN.

14. The apparatus of claim 13 where said two opposing pillars are composed of n-type GaN.

15. An apparatus comprising:

a single substrate;

a microchannel defined in the substrate;

at least one integrated peristaltic GaN micropump for pumping fluid to be analyzed, operatively and integrally formed about a corresponding portion of the microchannel in the substrate using photo-electro-chemical etch techniques (PEC), which corresponding portion comprises a pumping chamber of the peristaltic micropump;

a plurality of integrated analysis chambers communicated to the microchannel and hence to the pumping chamber of the at least one integrated peristaltic micropump; and a plurality of integrated analysis devices integrally manufactured into the substrate using nitride processes compatible with PEC and operatively communicated to the analysis chambers, where said micropump comprises:

an electro-deformable GaN membrane; a substrate disposed below said membrane and coupled thereto, a microchannel defined between said membrane and substrate, said microchannel having a longitudinal axis; and an electrode structure disposed on at least one side of said membrane along side of said microchannel, where said electrode structure is comprised of two opposing electrode substructures extending parallel to said microchannel.

16. The apparatus of claim 15 where said two opposing electrode substructures each comprise a plurality of discrete electrodes arranged and configured to provide pairs of opposing electrodes on each side of said microchannel.

* * * * *

UNITED STATES PATENT AND TRADEMARK OFFICE

CERTIFICATE OF CORRECTION

PATENT NO. : 7,189,358 B2
APPLICATION NO. : 09/923582
DATED : March 13, 2007
INVENTOR(S) : Robert A. Beach, Robert P. Strittmatter and Thomas C. McGill It is certified that error appears in the above-identified patent and that said Letters Patent is hereby corrected as shown below:

Col. 1, line 5 insert
--The U.S. Government has certain rights in this invention pursuant to Grant No. N00014-99-1-0972 awarded by the Office of Naval Research.--

Signed and Sealed this

Third Day of July, 2007

JON W. DUDAS
*Director of the United States Patent and Trademark Office*